(12) United States Patent
Gueugnaut et al.

(10) Patent No.: US 8,804,458 B2
(45) Date of Patent: Aug. 12, 2014

(54) NON DESTRUCTIVE TESTING DEVICE AND METHOD FOR DETECTING POSSIBLE ANOMALIES OF A WALL THICKNESS

(75) Inventors: Dominique Gueugnaut, Paris (FR); Stéphane Raze, Paris (FR); Daniel Chauveau, Aumont en Halatte (FR); Didier Flotte, Metz (FR)

(73) Assignees: GDF Suez, Courbevoie (FR); Institut de Soudure, Villepinte (FR)

( * ) Notice: Subject to any disclaimer, the term of this patent is extended or adjusted under 35 U.S.C. 154(b) by 684 days.

(21) Appl. No.: 13/089,347

(22) Filed: Apr. 19, 2011

(65) Prior Publication Data

US 2011/0255373 A1    Oct. 20, 2011

(30) Foreign Application Priority Data

Apr. 20, 2010   (FR) ...................... 10 53003

(51) Int. Cl.
  *G01S 15/00*   (2006.01)
(52) U.S. Cl.
  USPC ............................. 367/99; 73/639
(58) Field of Classification Search
  USPC ............................. 367/99; 73/639
  See application file for complete search history.

(56) References Cited

U.S. PATENT DOCUMENTS

| 4,202,216 A | | 5/1980 | Bull et al. | |
|---|---|---|---|---|
| 4,217,782 A | | 8/1980 | Pont | |
| 4,302,976 A | | 12/1981 | Bull | |
| 4,412,315 A | * | 10/1983 | Flournoy | ........................ 367/99 |
| 4,566,332 A | | 1/1986 | Collingwood | |
| 4,893,286 A | * | 1/1990 | Cobb | ............... 367/87 |
| 5,313,950 A | | 5/1994 | Ishikawa et al. | |
| 5,419,196 A | | 5/1995 | Havira et al. | |
| 6,772,636 B2 | * | 8/2004 | Lam et al. | ........................ 73/622 |

FOREIGN PATENT DOCUMENTS

DE    102004061870 B3    6/2006

* cited by examiner

*Primary Examiner* — Mark Hellner
(74) *Attorney, Agent, or Firm* — Harness, Dickey & Pierce, PLC

(57) ABSTRACT

The invention relates to a nondestructive testing device for detecting possible thickness anomalies (Ve) of a wall (P), this device comprising a sensor (1) including means (11) for emitting and receiving ultrasonic waves, and acoustic coupling means (2). The sensor according to the invention comprises a rigid enclosure (12, 13) sealingly defining a free internal volume (10), and the coupling means (2) comprise a solid coupling body (21) belonging to the enclosure, and a coupling liquid (L) disposed in the free internal volume (10) and in which the emitting and receiving means (11) soak.

12 Claims, 5 Drawing Sheets

NON DESTRUCTIVE TESTING DEVICE AND METHOD FOR DETECTING POSSIBLE ANOMALIES OF A WALL THICKNESS

FIELD

The invention generally relates to the techniques of non destructive testing.

BACKGROUND

According to a first aspect, the invention more particularly relates to a nondestructive testing device designed to detect possible thickness anomalies of a wall, this device including at least a sensor comprising emitting and receiving means designed to emit and receive ultrasonic waves along a direction selected from a set of directions including at least a first direction, and coupling means capable of transmitting, during operation, said ultrasonic waves at a surface of the wall to be tested.

Herein, what is meant by "thickness anomalies of a wall", are clean and local thickness variations of this wall, or compactness defects like stripes, cracks or notches.

Such a device is for example described in patent document GB 2,013,344.

The device described in this prior document is the subject matter of two different embodiments, of which only the first allows the emission of ultrasonic waves along a well controlled direction but have to be handled manually by an operator.

SUMMARY

In this context, the main object of the present invention is to provide a nondestructive testing device which can be implemented automatically and, at the same time, is sufficiently precise to allow an evaluation of the dimensions of the observed wall thickness anomalies. To this end, the device of the invention, which is further in accordance with the generic definition given thereto by the preamble above, is substantially characterized in that said sensor comprises a rigid enclosure sealingly defining a free internal volume, and in that the coupling means comprise a solid coupling body belonging to the enclosure, and a coupling liquid disposed in the free internal volume and in which the emitting and receiving means soak.

Thanks to this arrangement, the wall can be checked when "dry", i.e. the provision of a coupling liquid or gel between the sensor and the wall being needless.

An advantageous embodiment of the invention can be obtained by providing the sensor such that it comprises a stator and a rotor forming said enclosure, that the rotor be rotationally mounted, with respect to the stator, around an axis of rotation perpendicular to a plane containing each direction of said set, that the rotor and the stator sealingly define therebetween said free internal volume, that the emitting and receiving means be disposed in the internal volume and be fixed to the stator, and that the solid coupling body comprises a coupling ring, this coupling ring belonging to the rotor, being coaxial with the axis of rotation, and having said plane as a transverse plane, and the coupling liquid contributing with the emitting and receiving means to completely fill the internal volume, the ultrasonic waves propagating along said first direction thus traversing a first active zone of the periphery of the ring which depends on the relative angular position of the rotor and the stator, but which is fixed with respect to the stator.

For example, in a possible embodiment of the invention, the stator is provided such that it substantially comprises a shaft extending along the axis of rotation, that the rotor comprises, in addition to the coupling ring, two cheeks slipped on the shaft on both sides of the coupling ring, and that the sensor further comprises clamping means sealingly pressing the cheeks against the ring, two bearings each one being interposed between the shaft and one of the cheeks, and sealing members for sealing between the shaft and the cheeks.

The emitting and receiving means, which comprise for example one or more piezoelectric elements, can also comprise a reflector.

In an advantageous embodiment of the invention, the first direction forms with a radial direction an angle of 28 degrees, plus or minus 10 degrees.

Meanwhile, it is also possible to provide said set such that it further comprises at least a second direction, that this second direction forms with a radial direction an angle equal to, plus or minus 10 degrees, zero and that the ultrasonic waves propagate along the second direction traversing a second active zone of the periphery of the ring which may be the same as the first active zone, which depends on the relative angular position of the rotor and the stator, but which is fixed with respect to the stator.

Advantageously, the device of the invention can also comprise application means designed to apply, with a non null elastic force, a peripheral contact zone of the ring on the wall surface, to move, while applying it, the ring contact zone on the wall surface, and to cause each active zone of the ring to permanently coincide with at least part of the contact zone.

If the device of the invention is specifically designed to detect possible thickness anomalies of a tube wall having a longitudinal axis, it would be judicious to provide this device such that it comprises a carriage selectively movable in translation within the tube and on which the sensor is mounted, this carriage being provided with guiding means, for guiding said application means, and motor means, the guiding means being designed to make a longitudinal axis of the carriage coincide with the longitudinal axis of the tube, and that the application means substantially comprise eccentric means carried by the guiding means, carrying the sensor, rotationally movable with respect to the guiding means around the longitudinal axis of the carriage, and designed to rotationally drive the sensor around the longitudinal axis of the carriage by applying the contact zone of the ring on the internal surface of the tube wall, the motor means being designed to rotationally drive the eccentric means with respect to the guiding means.

The invention also relates to a non destructive testing method for detecting possible thickness anomalies of a cylindrical tube wall having a longitudinal axis, this method including a sensing step of testing the tube wall thickness by means of a sensor emitting and receiving ultrasonic waves, and being characterized in that the sensing step is carried out by means of operations of at least pressing the sensor on the internal surface of the tube, moving the sensor, while pressing it, along a path both tangential and longitudinal on the internal surface of the tube, for example along a helicoidal path, recording the ultrasonic waves received by the sensor after reflection and/or diffraction by the internal wall of the tube, and analyzing the received ultrasonic waves.

At least part of the ultrasonic waves emitted by the sensor are preferably directed so as to propagate in the tube wall along a direction forming with a radial direction of the tube an angle ranging between 30 degrees and 60 degrees.

At least part of the ultrasonic waves emitted by the sensor can also be directed so as to propagate in the tube wall along a direction forming with a radial direction of the tube an angle ranging between −15 degrees and +15 degrees.

Advantageously, the ultrasonic waves emitted by the sensor along any one of the above mentioned directions are longitudinal waves.

The operation of analyzing the ultrasonic waves received by the sensor preferably comprises operations of identifying two echoes originating from a same stripe or crack type defect, measuring a reception time difference of both echoes, and evaluating the height of the defect as a function of at least the nominal thickness of the tube wall, the speed of the ultrasonic waves in the wall tube, and the reception time difference of both echoes.

The testing method of the invention is particularly advantageous in the case where the tube is a fluid piping, and in particular a gas piping.

This method is in particular applicable in the case where the tube is made of vinyl polychloride, polyamide, or polyolefin, such as polyethylene or polypropylene.

DRAWINGS

Other characteristics and advantages of the invention will become more apparent from the following description thereof, made in an indicative and by no means restrictive way, with reference to the accompanying drawings, wherein.

DETAILED DESCRIPTION

The major elements illustrated on these figures and called upon in the present description are marked by references between brackets or not, the references between brackets being assigned to the sets to which the elements marked by references without brackets belong.

As previously stated, the invention relates to a nondestructive testing device designed to detect possible defects Ve (FIG. 5) each of which adopting the shape of a clean and local variation of the thickness E of a wall P, and has thus the form of a more or less broad crack or stripe.

In particular, the invention relates to a nondestructive testing device designed to detect possible defects affecting the wall P of cylindrical tubes T, which can be fluid piping, and in particular gas piping and/or which can be made of vinyl polychloride, polyamide, or polyolefin, such as polyethylene or polypropylene.

More particularly, this device comprises a sensor 1 and coupling means 2.

Figure 6:
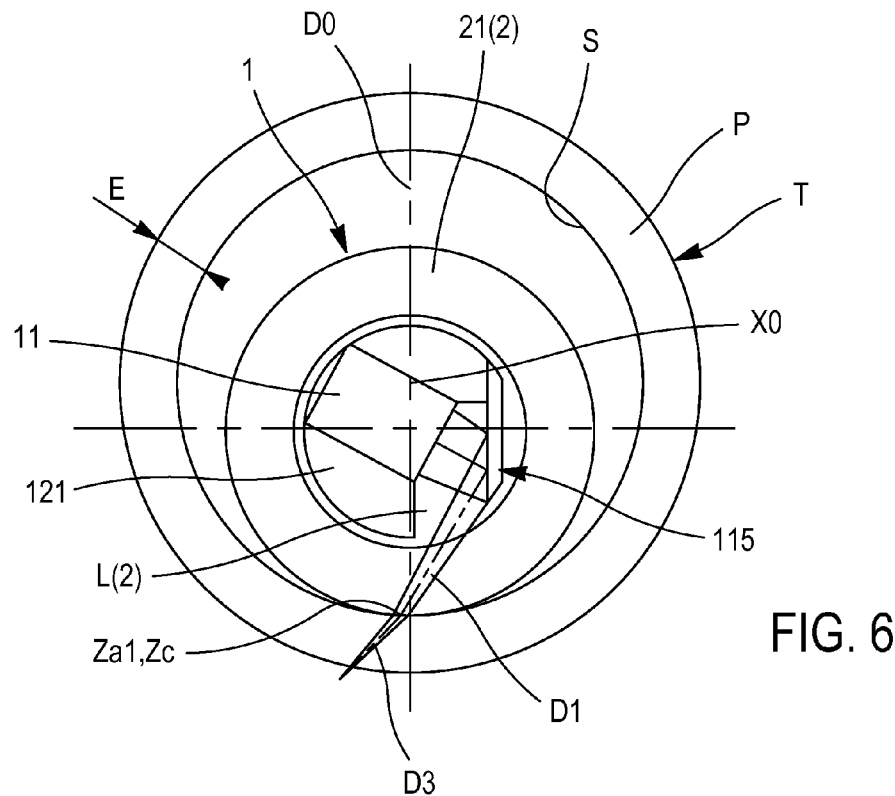
FIG. 6 is a schematic cross-sectional view of a sensor in accordance with the invention, represented in a tube, and emitting in this tube wall substantially nonradial ultrasonic waves.

Sensor 1 comprises emitting and receiving means 11 designed to emit and receive ultrasonic waves along one or more directions and more particularly along a first direction D1 (FIG. 6).

Figure 3:
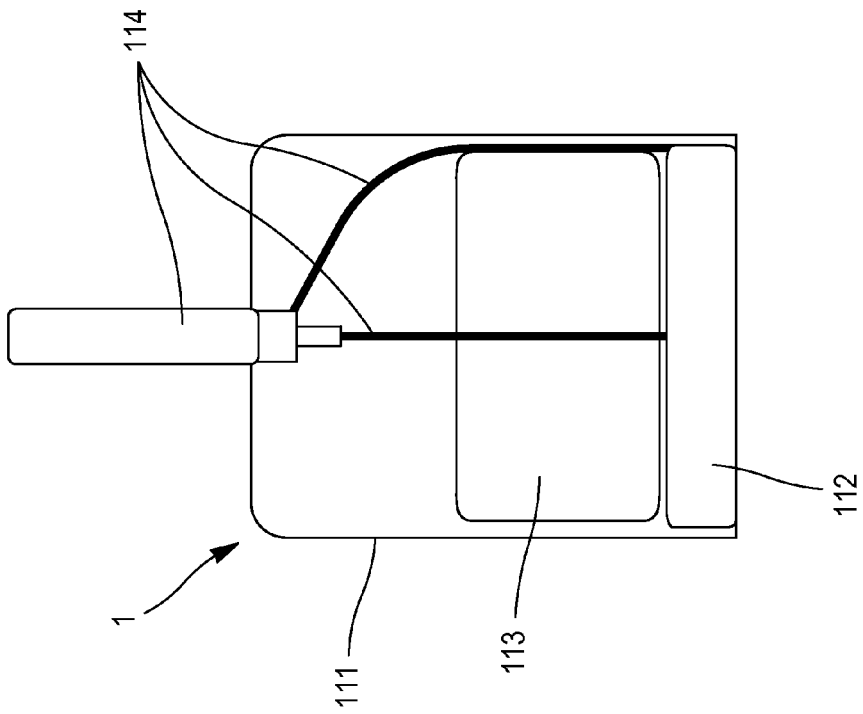
FIG. 3 is a schematic cross-sectional view of a translator that may be used in a sensor as illustrated in FIG. 1.
Figure 2:
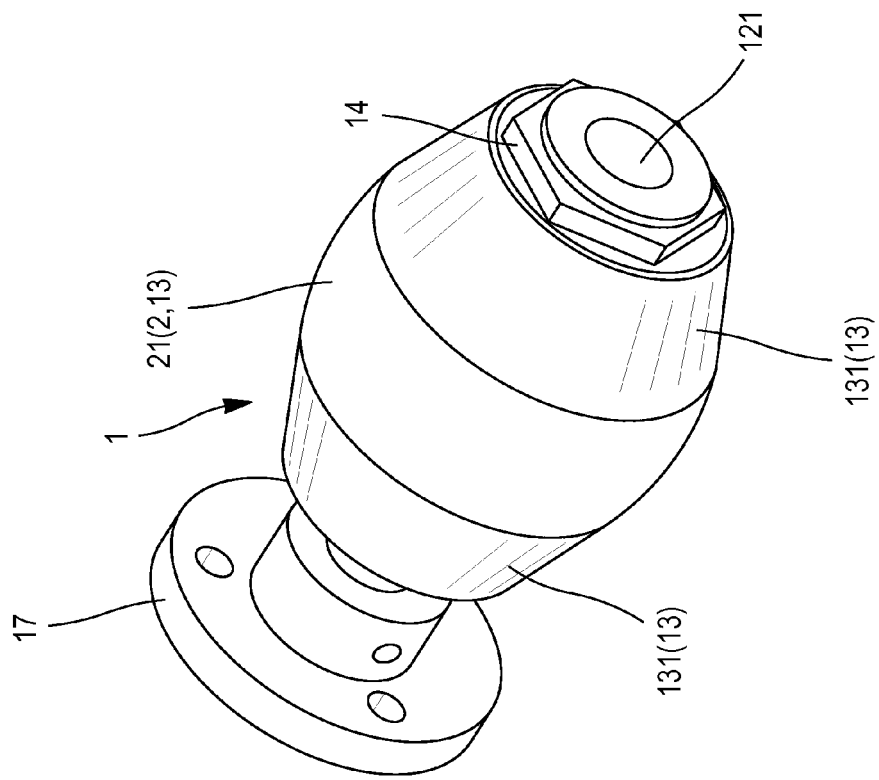
FIG. 2 is a perspective view, at a smaller scale, of the sensor illustrated on FIG. 1.

The emitting and receiving means 11, which are sufficiently known by a man skilled in the art so as not to require a detailed description, comprise for example (FIG. 3) a housing 111, one or more piezoelectric elements 112 accommodated in the housing, an acoustic absorbent 113 also accommodated in the housing, and an electric cable 114 making it possible to send an electrical excitation signal to each piezoelectric element 112 acting as an ultrasonic wave emitter, and/or to collect from each piezoelectric element 112 acting as an ultrasonic wave receiver an electrical signal representative of the acoustic waves received by this element.

With regard to the coupling means 2, they are designed to transmit, during operation, the ultrasonic waves to surface S of wall P of tube T to be tested.

Sensor 1 of the invention comprises a stator 12 and a rotor 13 (FIG. 1), this rotor 13 being rotationally mounted, with respect to stator 12, around an axis of rotation X.

Figure 1:
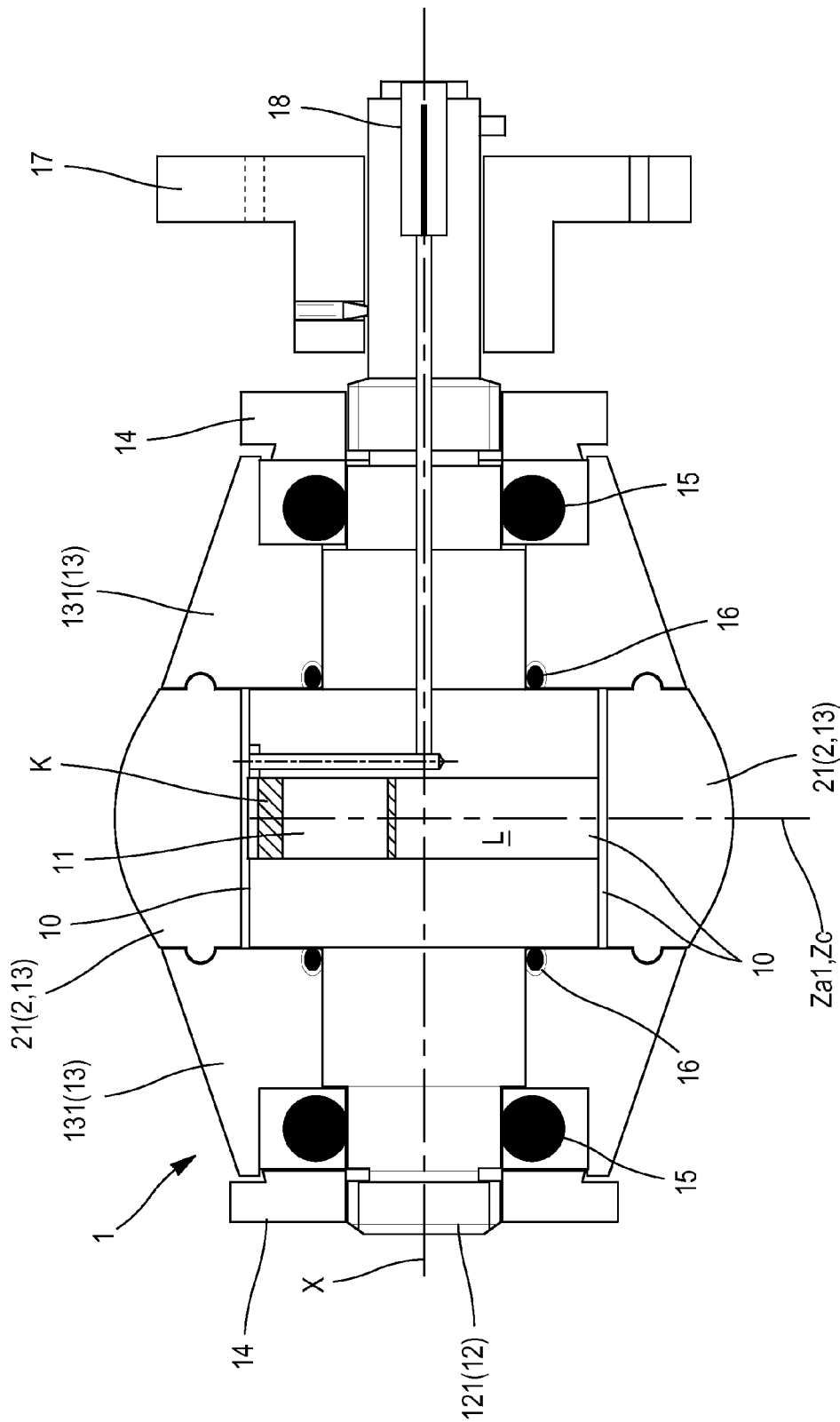
FIG. 1 is a schematic cross-sectional axial view of a sensor belonging to a device in accordance with the invention.

The one or more directions of emission of the emitted ultrasonic waves by means 11 exist(s) in a plane which is both perpendicular to the plane of FIG. 1 and perpendicular to the axis of rotation X of rotor 13 with respect to stator 12.

Rotor 13 and stator 12, which together constitute a rigid enclosure, sealingly define therebetween, a free internal volume 10 inside which the emitting and receiving means 11 are disposed.

These emitting and receiving means 11 are in addition fixed to stator 12, for example, by means of a glue pad K.

Inside internal volume 10, emitting and receiving means 11 soak in a coupling liquid L which belongs to the coupling means 2, which is, for example, composed of diluted ethylene glycol, and which contributes, along with the emitting and receiving means 11, to completely fill in the internal volume 10.

In addition to the coupling liquid L, the coupling means 2 comprise a coupling ring 21, which also belongs to rotor 13.

This ring 21 is coaxial with the axis of rotation X and has, as a transverse plane and, in fact, as a median plane as well, the above mentioned plane which is perpendicular to both the plane of FIG. 1 and to the axis of rotation X.

Thus, whatever their direction, the ultrasonic waves which are emitted by means 11 and which propagate along this direction traverse a so-called "active" zone, of the periphery of ring 21 which depends on the relative angular position of rotor 13 and stator 12, but which is fixed with respect to stator 12.

Figure 7:
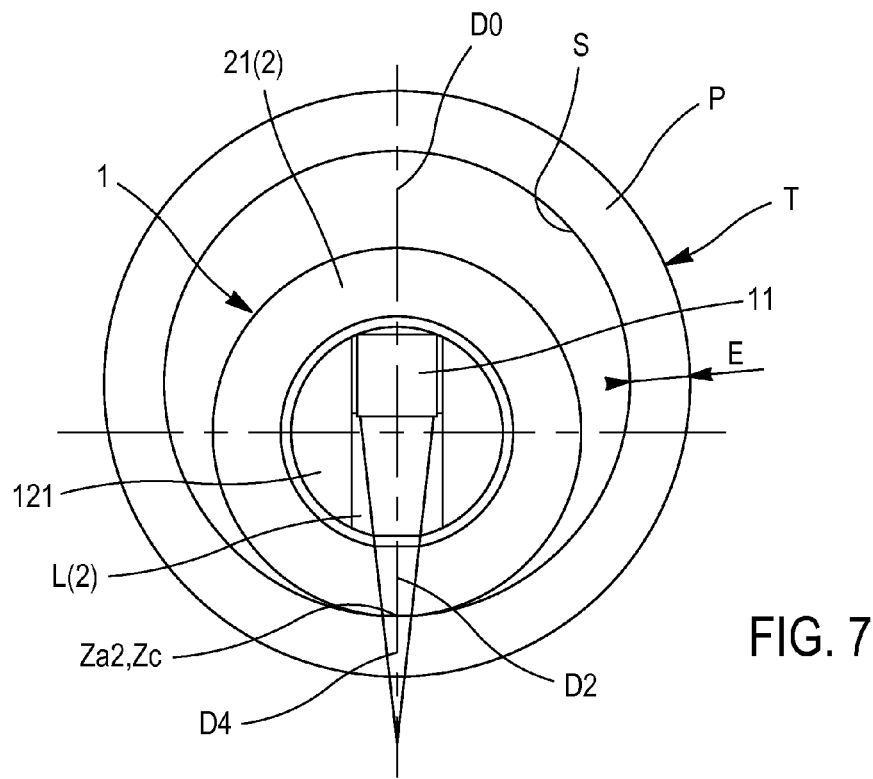
FIG. 7 is a schematic cross-sectional view of a sensor in accordance with the invention, represented in a tube, and emitting in this tube wall substantially radial ultrasonic waves.

In the case where the ultrasonic waves are emitted by means 11 along direction D1 illustrated in FIG. 6, the active zone of the ring periphery is denoted as Za1, and in the case where the ultrasonic waves are emitted by means 11 along direction D2 illustrated in FIG. 7, the active zone of the ring periphery is denoted as Za2.

Stator 12 substantially comprises a shouldered shaft 121, the shape of which being elongated along the axis of rotation X, and partially hollow in a transverse direction (see FIG. 1) so as to accommodate the emitting and receiving means 11.

Rotor 13 comprises, in addition to the coupling ring 21, two cheeks 131 slipped on shaft 121 on both sides of this coupling ring 21.

Sensor 1 further comprises clamping means of tightening 14, two bearings 15, and sealing members 16.

The function of clamping means 14, which are for example composed of two nuts fixed on corresponding threaded parts of shaft 121, is to sealingly press cheeks 131 against ring 21 along the direction of axis X.

The function of both bearings 15, each of which being interposed between the shaft 121 and one of cheeks 131, is to allow a free rotation of rotor 13 with respect to stator 12.

Finally, the function of the sealing members 16, which are for example composed of O-rings disposed between shaft 121 and both respective cheeks 131, is to ensure the sealing between this shaft 121 and the cheeks 131, and thus to more particularly ensure the containment of the coupling liquid L in the internal volume 10.

Figure 4:
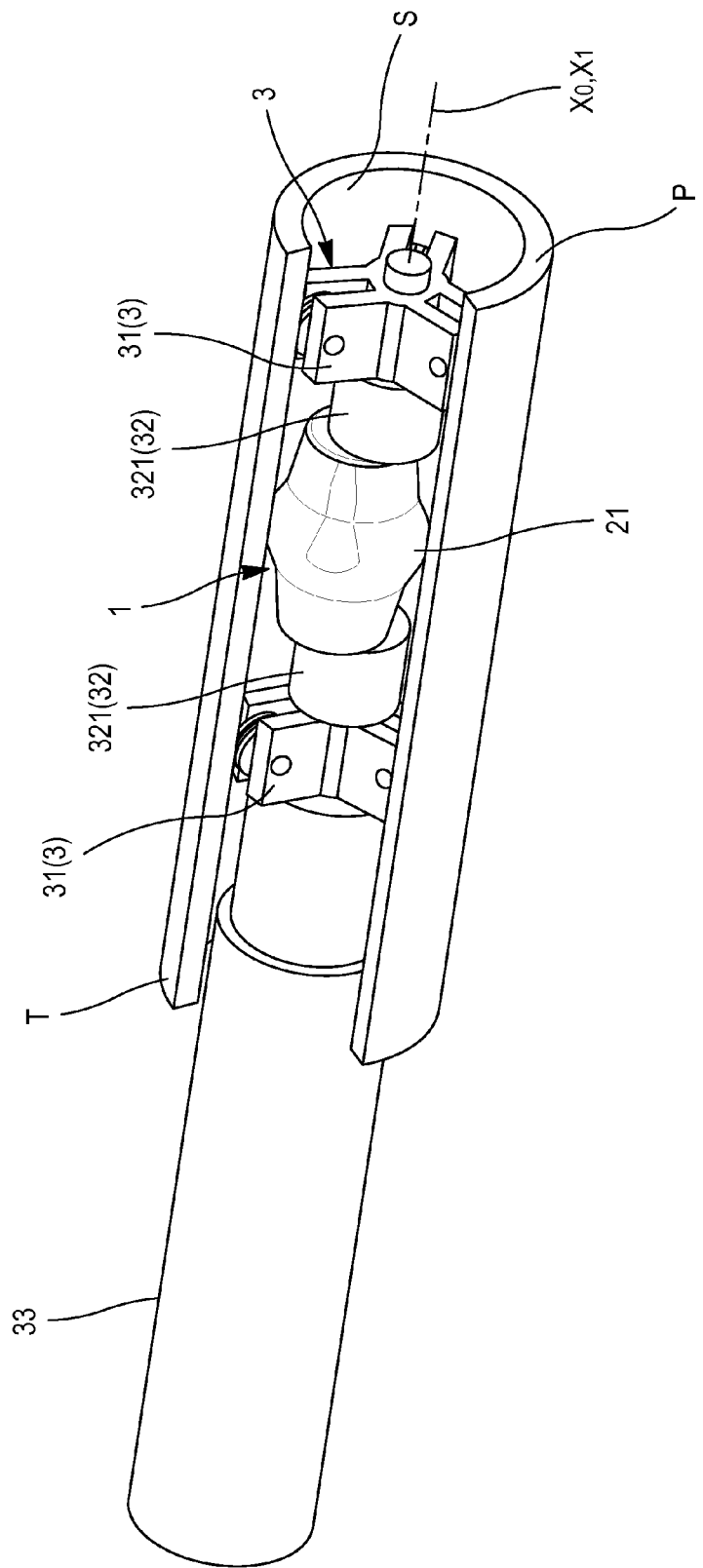
FIG. 4 is a perspective view of a device in accordance with the invention, inserted within a tube represented in a cutaway perspective.

As shown in FIG. 4, the testing device of the invention can advantageously comprise a carriage 3, on which sensor 1 is mounted, and which is designed to be inserted in tube T to be tested and to be movable therein in translation.

Preferably, this carriage 3 more particularly comprises guiding means 31, application means 32, and motor means 33.

The guiding means 31 are designed to cause the longitudinal axis X1 of carriage 3 coincide with the longitudinal axis X0 of tube T.

For example, these guiding means 31 comprise, as illustrated in FIG. 4, two rolling trains spaced apart from each other and each comprising three yokes disposed at 120 degrees from each other, each yoke carrying a wheel elastically applied on the internal surface S of tube T and able to roll without sliding on this internal surface T.

The application means 32 have several functions.

More specifically, these application means 32 are designed to apply, on one hand, with a non null elastic force, a peripheral contact zone Zc of ring 21 of sensor 1 on the surface S of wall P of tube T, and, on the other hand, to move, while applying it, the contact zone Zc of ring 21 on surface S of this wall P while rolling this ring on this surface, and finally, to make each active zone, such as Za1 or Za2, of coupling ring 21 permanently coincide with at least a part of the contact zone Zc.

As illustrated in FIG. 4, the application means 32 substantially comprise two eccentric means 321 each of which being journaled and fixed in axial translation with respect to one of the rolling trains 31.

Both eccentrics 321 are fixed, on both sides of sensor 1, at the corresponding ends of stator 12 of this sensor 1, for example by means of two corresponding flanges, such as flange 17 illustrated in FIG. 1 on only one side of the sensor for the sake of simplicity.

Each flange 17 is fixed in rotation with respect to shaft 121 of the sensor 1, so that the two eccentrics 321 are aligned together but are offset with respect to the axis X1 of carriage 3, around which these eccentrics are rotationally mounted together.

With regard to motor means 33, which for example comprise a stepping motor, they are designed to apply on eccentric means 321 a rotating controlled movement with respect to the rolling trains 31, around the longitudinal axis X1 of carriage 3.

In addition, each flange 17 can be provided with a device (not shown) designed to permanently provide data representative of the angular position of the contact zone Zc of ring 21 on wall P.

Thanks to this arrangement, eccentrics 321 thus rotationally drive, in operation, sensor 1 around the longitudinal axis X1 of carriage 3 by applying the contact zone Zc of the coupling ring 21 on the internal surface S of wall P of tube T.

The function of motor means 33 can also be that of driving the wheels of the rolling trains 31.

Alternatively, carriage 3 can be translated in tube T by means of a strip in which the electric cable 114 may be accommodated.

In both cases, sensor 1 is, during operation, moved on internal surface S of tube T along a helicoidal path and thus along both a tangential and longitudinal path, by rolling coupling ring 21 on surface S of this wall P, the contact zone Zc of this ring 21 being further applied with a non null elastic force on this surface S.

While this movement is carried out, the emitting and receiving means 11 emit ultrasonic waves which pass by at least one of the active zones Za1 and Za2 of the periphery of coupling ring 21.

The ultrasonic waves which result from the reflection and/or diffraction of the incident waves by the internal wall S of tube T and which are received back by sensor 1 are, after conversion in the form of electrical signals by means 11 and transmission over cable 114, recorded outside the tube by a suitable apparatus, then analyzed.

In the case where the electrical signals produced by means 11 in response to the ultrasonic waves received back are transmitted by land line, these signals for example pass by a connector 18 provided on shaft 121 (FIG. 1) and by a turning connector (not shown) embedded into eccentric 321.

Alternatively, these electrical signals can be transmitted via radio link.

Since, on one hand, the active zones Za1 and Za2 of the periphery of the coupling ring 21 are rotationally fixed around axis X with respect to the emitting and receiving means 11, thus also with respect to shaft 121 to which means 11 are fixed, since on the other hand flanges are rotationally fixed around axis X with respect to shaft 121, and finally since eccentrics 321 are rotationally fixed around axis X with respect to flanges 17, suitably indexing flanges 17 with respect to shaft 121 would be sufficient so that at least one of the active zones Za1 and Za2 of the periphery of the coupling ring 21 lays in the contact zone Zc of this ring 21 with surface S of wall P of tube T.

In practice, it is possible to superimpose the active zones Za1 and Za2, for example by using a multi-element piezoelectric transceiver making it possible to emit acoustic waves along an adjustable direction.

It is also possible to use a pair of sensors 1 the first one of which comprises means 11 for emitting and receiving ultrasonic waves along direction D1 (FIG. 6) and the second one of which comprises means 11 for emitting and receiving ultrasonic waves along direction D2 (FIG. 7), to make the active zone Za1 of ring 21 of the first sensor coincide with the contact zone Zc of this ring, and to make the active zone Za2 of ring 21 of the second sensor coincide with the contact zone Zc of this ring.

It is still possible to attach, in the same sensor 1, means 11 for emitting and receiving ultrasonic waves along direction D1 and means 11 for emitting and receiving ultrasonic waves along direction D2, the ring 21 of this sensor thus exhibiting two contact zones Zc also attached to each other.

As shown in FIG. 6, it can be judicious, in order to reduce the encumbrance of sensor 1, to provide the emitting and receiving means 11 with an acoustic reflector 115 in the case where the ultrasonic waves emitted and received by these means 11 advance according to a direction D1 which substantially deviates from the radial direction D0.

The ultrasonic waves used are preferably longitudinal waves, in a frequency range between 2 MHz and 15 MHz, and preferably around 5 MHz.

As shown in FIGS. 6 and 7, the emitted ultrasonic waves can be focused so as to converge onto a point located beyond the external surface of wall P of the tube T, the device of the invention being usable for all tubes of a range of tubes having different wall thicknesses E.

It is also judicious to provide (FIG. 6) direction D1, which is the privileged direction for emitting the ultrasonic waves, such that it forms with the radial direction D0 an angle of 28 degrees, more or less 10 degrees, i.e. an angle ranging between 18 and 38 degrees.

Under these conditions, these ultrasonic waves are propagated into wall P of tube T according to a direction D3 forming with the radial direction D0 of tube T an angle A1 ranging between 30 degrees and 60 degrees and preferably equal to 45 degrees.

In the case where ultrasonic waves are also emitted along another direction D2 (FIG. 7), this other direction D2 can form, with the radial direction D0, an angle equal to zero, more or less 10 degrees, i.e. an angle ranging between −10 degrees and +10 degrees.

Under these conditions, these ultrasonic waves propagate in wall P of tube T along a direction D4 forming with the radial direction D0 of tube T, an angle ranging between −15 degrees and +15 degrees.

Figure 5:
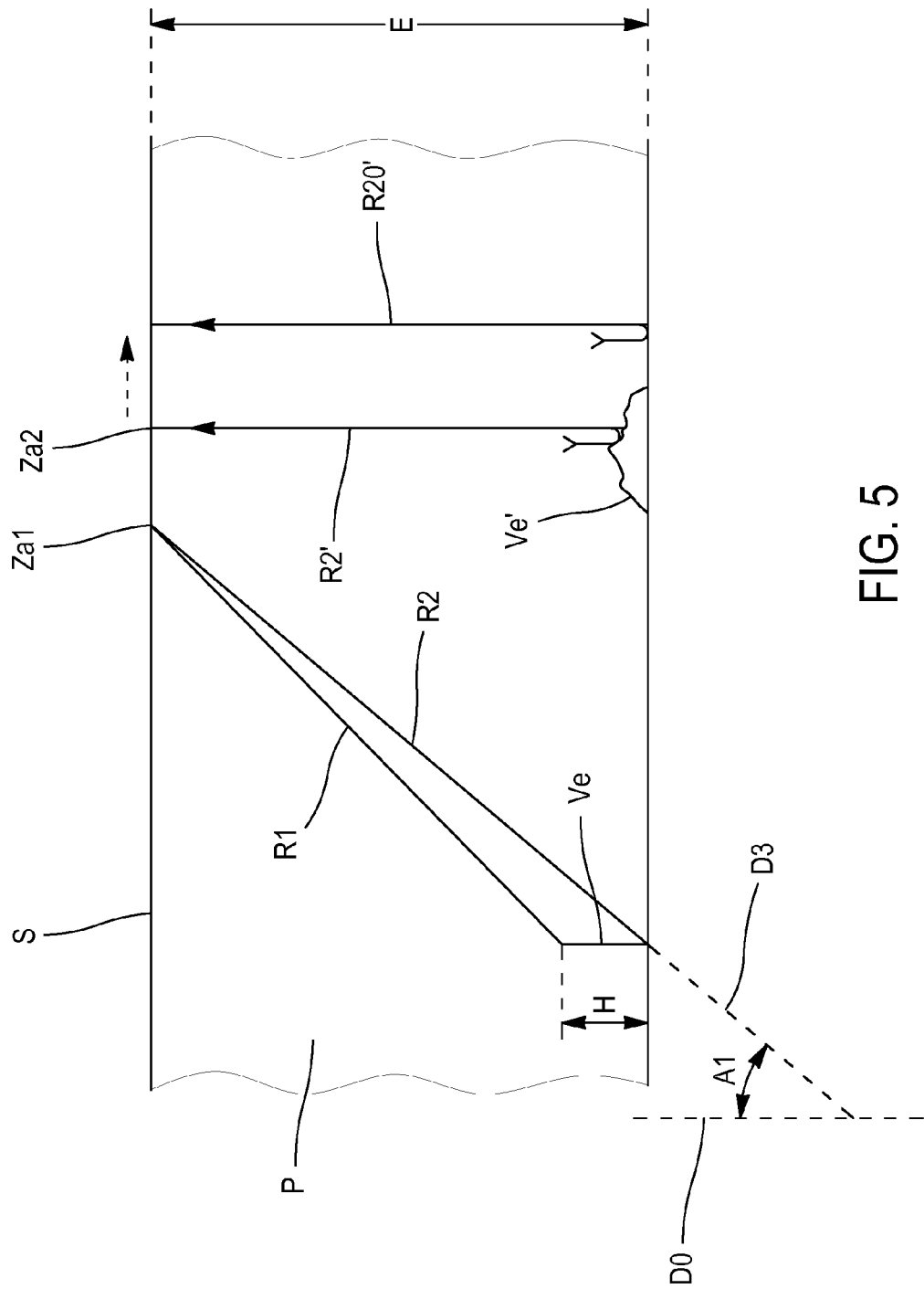
FIG. 5 is an enlarged cross-sectional view of a wall, considered as plane for the sake of simplicity, and having a crack and a compactness defect, this figure further schematically illustrating both echoes returned by these standard damages.

FIG. 5 is a schematic view of the modalities of analyzing the ultrasonic waves received by sensor 1 in the case where these waves meet a defect Ve illustrated on the left typically composed of a stripe or crack on the external surface of the wall P of tube T, and ultrasonic waves received by sensor 1 in the case where these waves meet a defect Ve' illustrated on the right and typically composed of a compactness defect.

Although, for the sake of simplicity, this wall is illustrated as plane in FIG. 5, and although the device of the invention may be used on plane walls, a man skilled in the art will appreciate that the schematic representation of FIG. 5 is applicable to a cylindrical wall.

As shown on this figure, the ultrasonic waves which are emitted by the active zone Za1 and which meet a crack or stripe type defect Ve produce two echoes R1 and R2, which are captured one after the other in this order by the active zone Za1.

The first echo R1, of weaker amplitude, originates from the diffraction of the ultrasonic waves by the top of defect Ve.

The second R2 echo, of higher amplitude, is caused by a corner effect by which the ultrasonic waves are reflected by the base of defect Ve.

The difference of respective reception times of these two echoes R1 and R2 in the active zone Za1 is linked, via laws known to the man skilled in the art, to angle A1, defect height H, nominal thickness E of wall P, and to the propagation velocity of the ultrasonic waves in this wall.

Insofar as the propagation velocity of the ultrasonic waves in a defectless wall can be easily determined through experiment and calibration carried beforehand, and where the difference in reception time of echoes R1 and R2 is measured, the height H of the defect Ve can thus be determined on the basis of the other above mentioned ones, which are all known.

As further shown on the right of FIG. 5, the ultrasonic waves which are emitted by the active zone Za2 and which meet a compactness type defect Ve' produce an echo R2', which is captured by the active zone Za2 earlier than echo R2'0 illustrated more on the right and returned by a wall free from any anomaly.

Insofar as the difference of respective reception times of these two echoes R2' and R2'0 in the active zone Za2 relates to the defect height and to the propagation velocity of the ultrasonic waves in wall P, the defect height may also be determined from this reception time difference.

The invention claimed is:

1. A nondestructive testing device for detecting possible thickness anomalies of a wall, such device comprising at least one sensor assembly including a sensor for emitting and receiving ultrasonic waves along a direction selected from a set including at least a first direction, and a coupling element for transmitting, in operation, said ultrasonic waves to a surface of the wall to be tested, wherein said sensor assembly comprises a rigid enclosure sealingly defining a free internal volume, wherein the coupling element comprises a solid coupling body belonging to the enclosure, and a coupling liquid disposed in the free internal volume and in which the sensor soaks, wherein the sensor assembly comprises a stator and a rotor forming said enclosure, wherein the rotor is mounted rotatable, with respect to the stator, around an axis of rotation perpendicular to a plane including each direction of said set, wherein the rotor and the stator sealingly define therebetween said free internal volume, wherein the sensor is disposed within the internal volume and fixed to the stator, wherein the solid coupling body comprises a coupling ring, said coupling ring belonging to the rotor, being coaxial with the axis of rotation, and having said plane as a transverse plane, and the coupling liquid contributing with the sensor assembly to completely fill in the internal volume, the ultrasonic waves propagating along said first direction thus traversing a first active zone of the periphery of the ring which depends on the relative angular position of the rotor and the stator, but which is fixed with respect to the stator, wherein said device further comprises a plurality of spaced apart eccentrics for applying with a non null elastic force a peripheral contact zone of the ring onto the surface of the wall, to move, while applying it, the contact zone of the ring on the surface of the wall, and to cause each active zone of the ring permanently coincide with at least part of the contact zone, wherein said device, which is designed to detect possible thickness anomalies of the wall of a tube having a longitudinal axis, further comprises a carriage selectively movable in translation in the tube and on which the sensor is mounted, this carriage being provided with a plurality of spaced apart trains, with said plurality of eccentrics, and with a motor, wherein the trains are designed to cause a longitudinal axis of carriage to coincide with the longitudinal axis of the tube, and wherein the eccentrics are carried by the stator, carrying the sensor, rotationally movable with respect to the longitudinal axis of the carriage, and designed to rotationally drive said sensor around the longitudinal axis of the carriage by applying the contact zone of the ring on the internal surface of the wall of tube, and the motor being designed to rotationally drive the eccentrics with respect to the trains.

2. The nondestructive testing device according to claim 1, wherein the stator substantially comprises a shaft extending along the axis of rotation, wherein the rotor comprises, in addition to the coupling ring, two cheeks slipped on the shaft on both sides of the coupling ring, and wherein the sensor further comprises clamps sealingly pressing the cheeks against the ring, two bearings one of which is interposed between the shaft and one of the cheeks, and sealing members for sealing between the shaft and the cheeks.

3. The nondestructive testing device according to claim 1, wherein the sensor assembly further comprises a reflector.

4. The nondestructive testing device according to claim 1, wherein said first direction forms with a radial direction an angle of 28 degrees, more or less 10 degrees.

5. The nondestructive testing device according to claim 1, wherein said set further comprises at least a second direction, wherein this second direction forms with a radial direction an angle of which value is, plus or minus 10 degrees, equal to zero and wherein the ultrasonic waves propagating along the second direction traverse a second active zone of the periphery of the ring which may be the same than the first active zone, which depends on the relative angular position of the rotor and the stator, but which is fixed with respect to the stator.

6. A non destructive testing method for detecting possible thickness anomalies of the wall of a cylindrical tube having a longitudinal axis, this method including a sensing step of testing the thickness of the wall of tube by means of a sensor emitting and receiving ultrasonic waves, wherein the sensing step is carried out by means of the operations of at least pressing the sensor on the internal surface of the tube, moving the sensor, while pressing it, along a path both tangential and longitudinal on the internal surface of the tube, recording the ultrasonic waves received by the sensor after reflection and/or diffraction by the internal wall of the tube, and analyzing the received ultrasonic waves, and wherein the operation of analyzing the ultrasonic waves received by the sensor comprises operations of identifying two echoes originating from a same stripe or crack type defect, measuring a difference in reception time of these two echoes, and evaluating the height of defect as a function of at least the nominal thickness of the wall of tube, the speed of the ultrasonic waves within the wall of tube, and the difference in reception time of both echoes.

7. The non destructive testing method according to claim 6, wherein at least part of the ultrasonic waves emitted by the sensor propagate in the wall of tube along a direction forming with a radial direction of tube an angle ranging between 30 degrees and 60 degrees.

8. The non destructive testing method according to claim 6, wherein at least part of the ultrasonic waves emitted by the sensor propagate within wall of tube along a direction forming with a radial direction of tube an angle ranging between −15 degrees and +15 degrees.

9. The non destructive testing method according to claim 6, wherein the ultrasonic waves emitted by the sensor are longitudinal waves.

10. The non destructive testing method according to claim 6, wherein the tube is a fluid piping, and more particularly gas piping.

11. The non destructive testing method according to claim 6, wherein the tube is made from vinyl polychloride, polyamide, or polyolefin, such as polyethylene or polypropylene.

12. The non destructive testing method according to claim 6, being implemented by the nondestructive testing device according to any one of claims 1 to 5.

* * * * *